United States Patent [19]

Kutner et al.

[11] Patent Number: 5,516,495
[45] Date of Patent: May 14, 1996

[54] CASE FOR USE IN DISINFECTING SOFT CONTACT LENSES

[75] Inventors: Barry S. Kutner, Wilton; Daniel A. Latowicki, Newtown, both of Conn.; Kenneth E. Malech, Briarcliff Manor, N.Y.

[73] Assignee: Flexiclave, Inc., Briarcliff, N.Y.

[21] Appl. No.: 383,571

[22] Filed: Feb. 3, 1995

Related U.S. Application Data

[63] Continuation-in-part of Ser. No. 16,581, Feb. 10, 1993, Pat. No. 5,387,404, which is a continuation-in-part of Ser. No. 835,309, Feb. 4, 1992, Pat. No. 5,248,748, which is a continuation-in-part of Ser. No. 692,736, Apr. 29, 1991, Pat. No. 5,413,757, which is a continuation-in-part of Ser. No. 184,246, Apr. 21, 1988, Pat. No. 5,019,344.

[51] Int. Cl.⁶ .............................. A61L 2/12; A45C 11/04
[52] U.S. Cl. .................. 422/300; 206/5.1; 134/901; 219/729; 219/736; 422/102; 422/21; 422/297; 422/301
[58] Field of Search ................... 422/297, 300, 422/301, 21, 102; 219/729, 736; 206/5.1; 134/901

[56] References Cited

U.S. PATENT DOCUMENTS

| | | | |
|---|---|---|---|
| 3,695,280 | 10/1972 | Sturgeon | 206/5.1 |
| 4,328,890 | 5/1982 | Thomas et al. | 206/5.1 |
| 4,582,076 | 4/1986 | Prat | 422/300 |
| 4,782,946 | 11/1988 | Pollak | 206/5.1 |
| 5,039,495 | 8/1991 | Kutner et al. | 422/299 |
| 5,101,967 | 4/1992 | Sibley | 206/5.1 |
| 5,164,166 | 11/1992 | Stepanski et al. | 422/297 |

*Primary Examiner*—Robert J. Warden
*Assistant Examiner*—Hien Tran
*Attorney, Agent, or Firm*—Steinberg, Raskin, & Davidson

[57] ABSTRACT

A case for use in disinfecting soft contact lenses including a pair of lens-receiving compartments formed by a first pair of substantially dome-shaped members mounted on a first cover member and a second pair of substantially dome-shaped members mounted on a second cover member. The dome-shaped members shield the interior of the lens-receiving compartments from microwave radiation when the case is used in a heat disinfecting process in which microwave radiation is utilized. The dome-shaped members of the first and second pairs are adapted to be brought into contiguous relationship to thereby form the pair of compartments.

11 Claims, 5 Drawing Sheets

FIG. 2
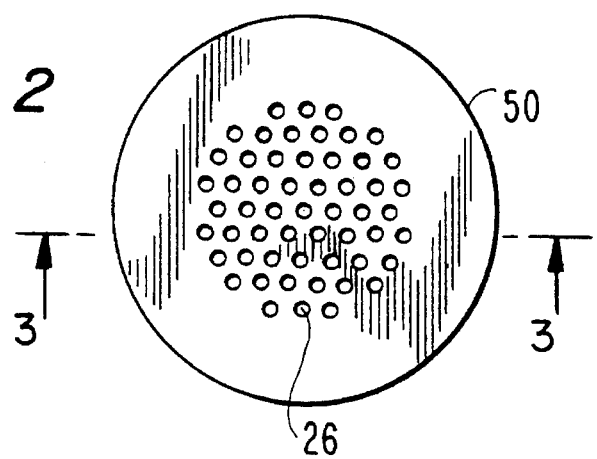
FIG. 3
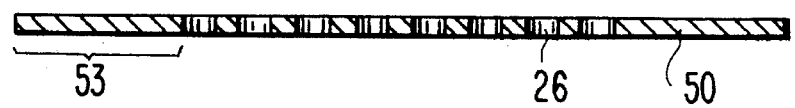
FIG. 4
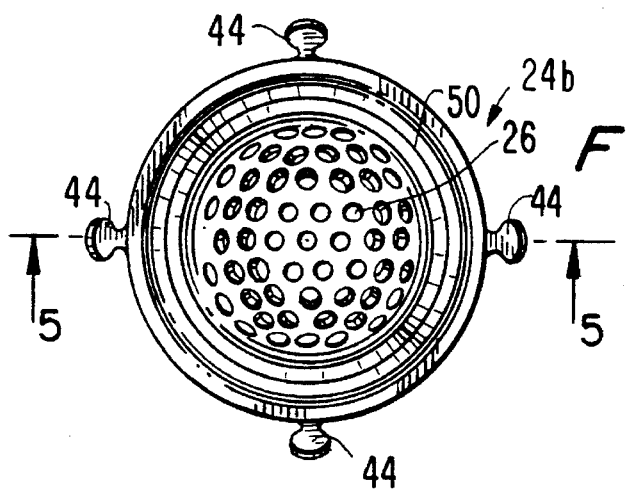
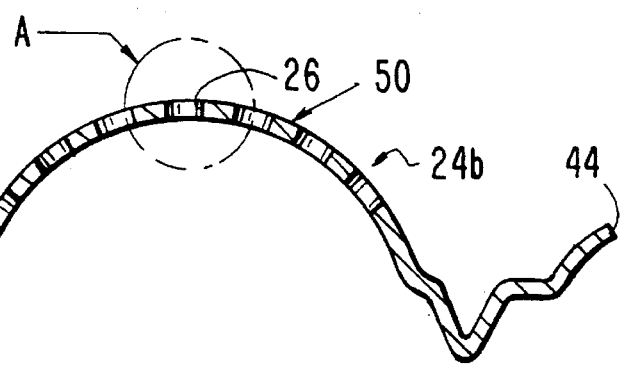
FIG. 5

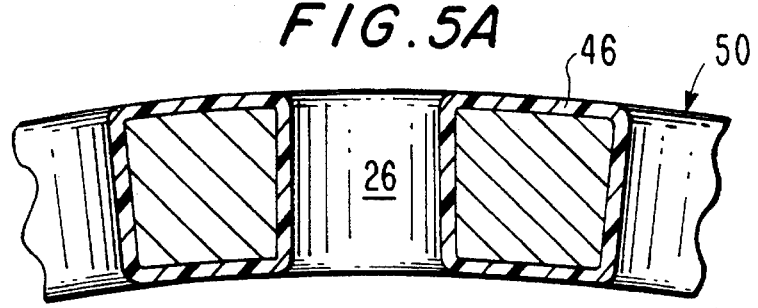
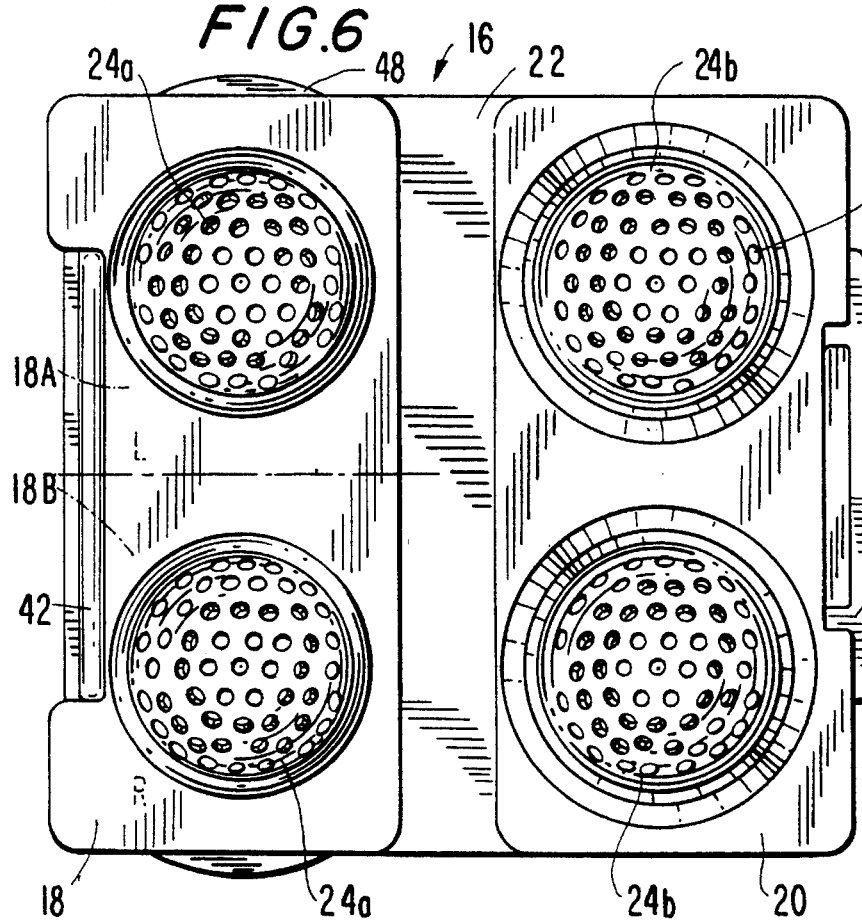
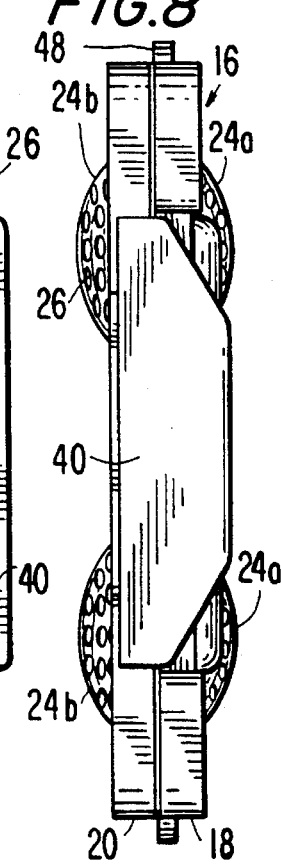

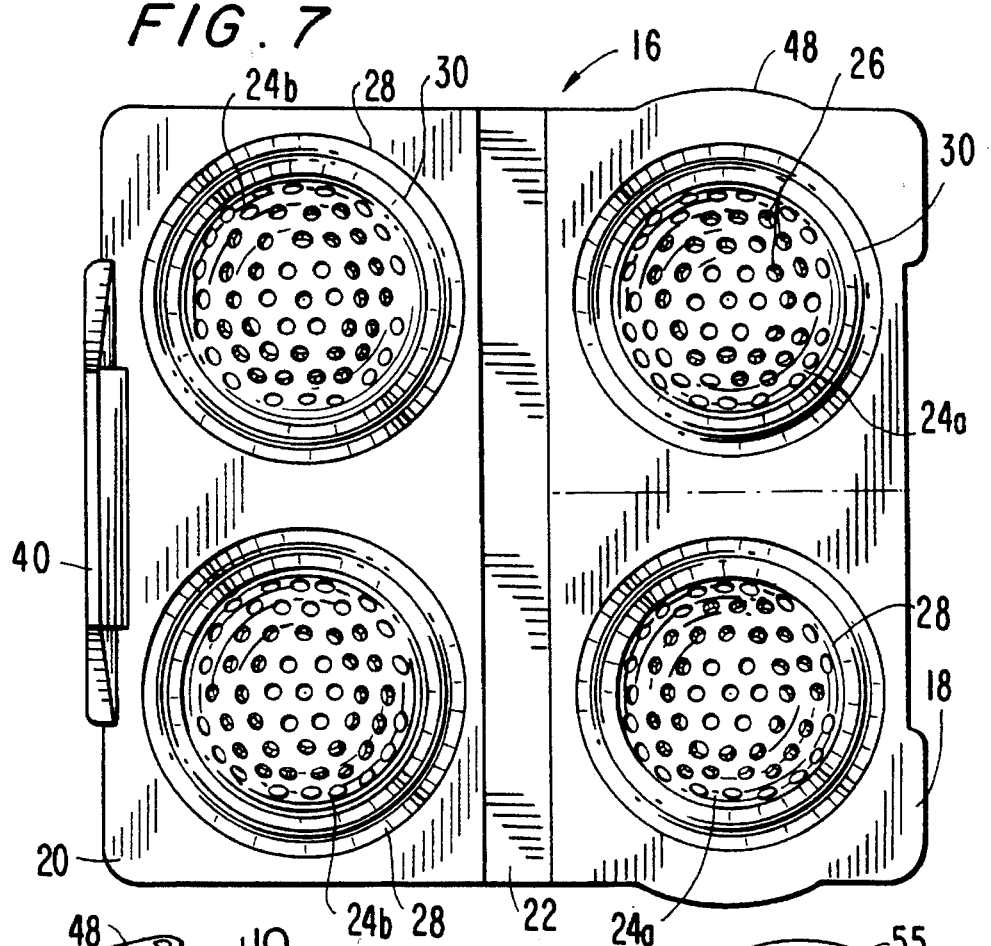
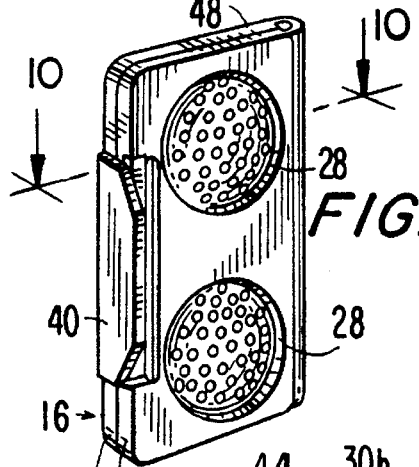
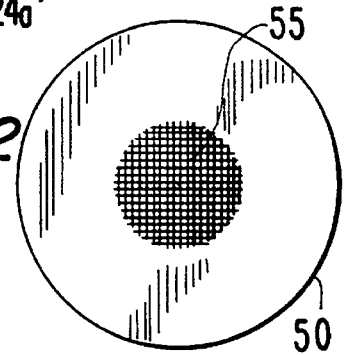
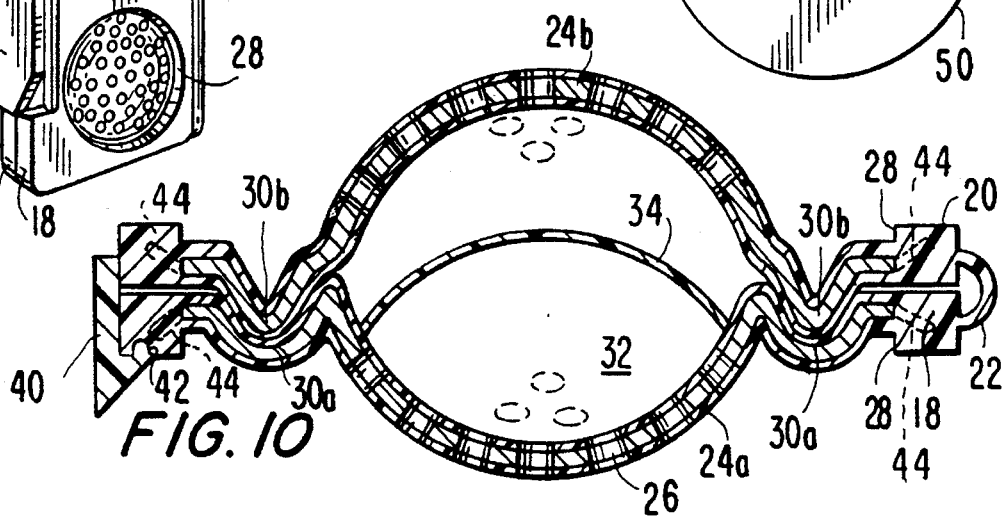

CASE FOR USE IN DISINFECTING SOFT CONTACT LENSES

This is a continuation-in-part of application Ser. No. 08/016,581 filed on Feb. 10, 1993, now U.S. Pat. No. 5,387,404, which in turn is a continuation-in-part of application Ser. No. 07/835,309 filed Feb. 4, 1992 now U.S. Pat. No. 5,248,748, which in turn is a continuation-in-part of application Ser. No. 07/692,736, filed Apr. 29, 1991, now U.S. Pat. No. 5,413,757, which in turn is a continuation-in-part of application Ser. No. 07/184,246, filed Apr. 21, 1988, now U.S. Pat. No. 5,019,344.

BACKGROUND OF THE INVENTION

This invention relates generally to a case for holding soft contact lenses and, more particularly, to a case for holding soft contact lenses during heat disinfection processes.

In caring for hydrophilic gel (soft) contact lenses, attention must be directed toward, among other things, maintaining lens hydration and protecting the lenses from pathogens. Exposure of soft contact lenses to heat or to the action of soaking solutions are the techniques used to provide the disinfection necessary to protect soft contact lenses from pathogens.

Disinfecting lenses by soaking in germicidal solutions is a two step process which includes soaking the lenses in the solution until the lens is disinfected, and then rinsing the lenses with a rinsing solution prior to insertion. Typically, lenses are stored in a germicidal solution, such as one that derives its germicidal activity from thimerosal or chlorhexidine, for at least four hours and then are rinsed in a saline solution. Such techniques are time consuming, require the user to keep different solutions on hand, and risk eye irritation should the disinfecting solution not be adequately rinsed from the lenses.

For heat disinfection, it is generally necessary to heat soft contact lenses to a temperature of 80° C. for at least 10 minutes. To insure lens hydration, the gel lenses are immersed in saline solution in their storage case which is then placed within a boiling unit. Although gel lenses can be disinfected in a shorter time by heat than by soaking, conventional heat disinfection techniques require a separate heating unit which adds to the expense of lens care. Moreover, in practice, heat disinfection of lenses is a relatively time-consuming procedure which necessitates that the wearer use an alternate pair of lenses, or eyeglasses, while disinfection proceeds.

OBJECTS AND SUMMARY OF THE INVENTION

It is an object of the present invention to provide new and improved case for holding soft contact lenses during disinfection.

Another object of the present invention is to provide new and improved case for holding soft contact lenses during a heat disinfection processes in which microwave radiation is utilized.

Briefly, in accordance with the present invention, these and other objects are attained by a providing a case for use in soft contact lens disinfecting processes which comprises means forming at least one contact lens-receiving compartment having an interior in fluid communication with the ambient atmosphere and means for shielding a contact lens situated in the compartment from microwave electromagnetic radiation. Preferably, the compartment-forming means form a pair of contact lens-receiving compartments, one for each of the left and right contact lenses. The compartment-forming means may comprise the shielding means, e.g., the compartment-forming means may be formed of apertured metallic sheet material whereby the apertures are sufficiently small to prevent passage of microwave electromagnetic radiation therethrough. The apertures also provide fluid communication between the interior of the contact lens-receiving compartment and the ambient atmosphere.

In a preferred embodiment, the compartment-forming means comprise a first pair of substantially dome-shaped members mounted on a first cover member, and a second pair of substantially dome-shaped members mounted on a second cover member. The dome-shaped members of the first and second pairs are adapted to be brought into mating engagement with each other to thereby form a pair of compartments for receiving a pair of contact lenses. The dome-shaped members are formed of apertured metallic sheet material or metallic wire mesh material to provide microwave shielding.

The first cover member may be in the form of two independent parts, each of which is designed to cover a respective dome-shaped member mounted on the second cover member, so that left and right contact lenses stored in each of the compartments can be separately accessible. Either cover member may be labelled appropriately to indicate the compartment which retains the left or right contact lenses.

The case is designed for use in a heat disinfecting process using microwave radiation described in U.S. Pat. No. 5,248,478 and pending application Ser. No. 08/016,581 filed Feb. 10, 1993. Briefly, a disinfecting solution is introduced into a vessel that is at least partially formed of material transparent to microwave electromagnetic radiation, the soft contact lenses are placed into the case, whereupon the case is introduced into an interior portion of the vessel, either before or after the disinfecting solution has been introduced, such that the contact lenses are placed into contact with the disinfecting solution. The vessel is closed and then subjected to microwave electromagnetic radiation to heat the disinfecting solution with which the lenses are in contact, while the lenses themselves are shielded from the radiation by the microwave shielding means. Irradiation continues until the lenses are disinfected. Reference is made to co-pending application Ser. No. 08/016,581 for a more detailed description of a suitable vessel and heat disinfection processes in which the case may be utilized.

BRIEF DESCRIPTION OF THE DRAWINGS

A more complete appreciation of the present invention and many of the attendant advantages thereof will be readily understood by reference to the following detailed description when considered in connection with the accompanying drawings in which:

FIG. 2 is a top plan view of a disc member prior to formation into a dome-shaped member comprising a component of a lens case in accordance with the invention;

FIG. 3 is a cross-sectional view taken along line 3—3 of FIG. 2;

FIG. 4 is a top plan view of a dome-shaped member formed from the disc shown in FIG. 2 and comprising a component of a lens case in accordance with the invention;

FIG. 5 is a cross-sectional view taken along line 5—5 of FIG. 4;

FIG. 5A is an enlarged detailed view of the region of the dome-shaped member shown in FIG. 5 designated "A";

FIG. 6 is a top plan view of a lens case in accordance with the invention in its open position;

FIG. 7 is a bottom plan view of the lens case illustrated in FIG. 6 in its open position;

FIG. 8 is a side elevation view of the lens case illustrated in FIG. 6 in its closed position;

FIG. 9 is a perspective view of the lens case shown in FIG. 8 in its closed position;

FIG. 10 is a cross-sectional view taken along line 10—10 of FIG. 9 and showing a contact lens situated in a respective compartment of the lens case;

FIG. 12 is a top plan view of another embodiment of a disc member prior to formation into a dome-shaped member comprising a component of a lens case in accordance with the invention.

DESCRIPTION OF THE PREFERRED EMBODIMENTS

Figure 1:
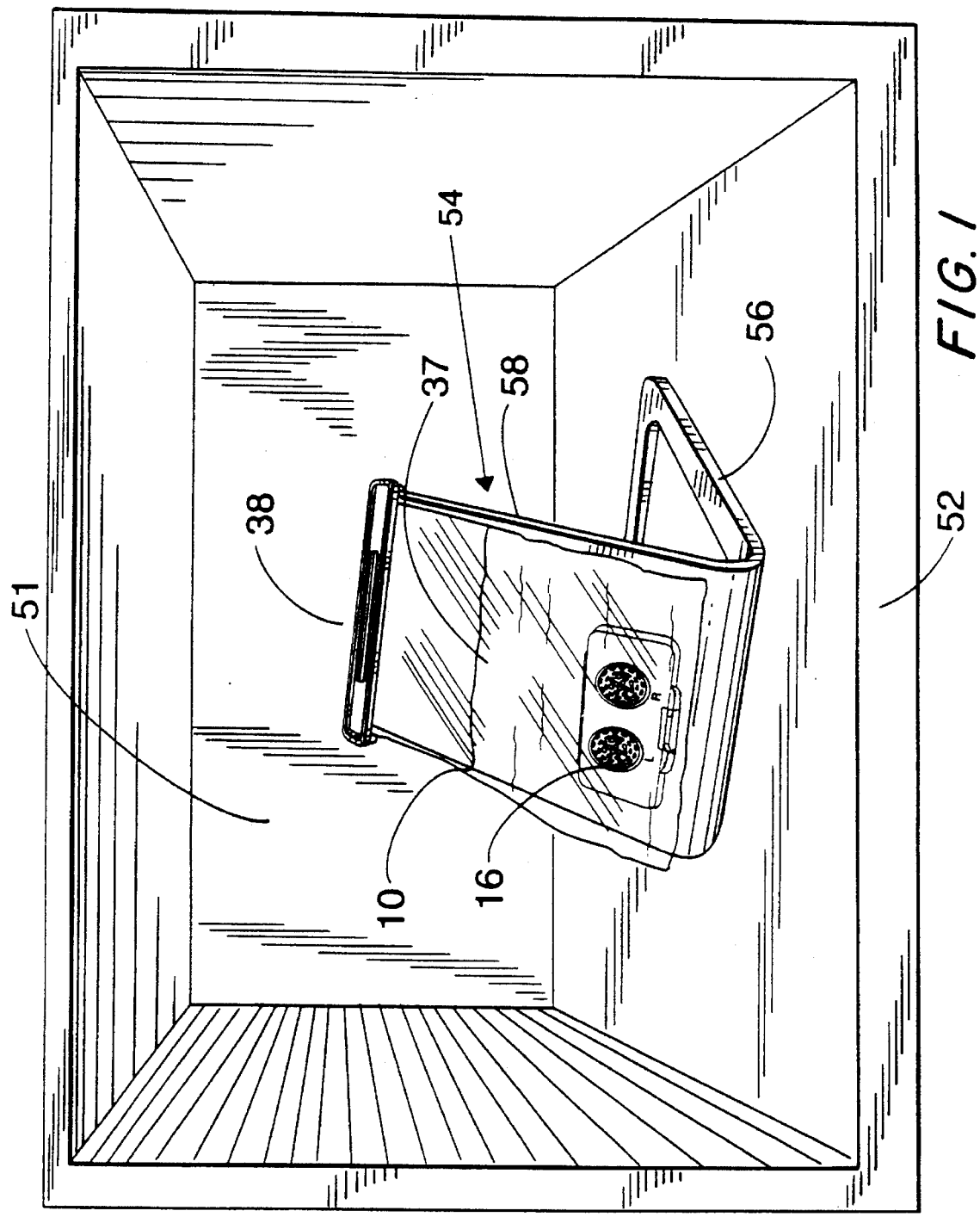
FIG. 1 is an orthogonal view of an assembly used during a microwave disinfecting process including a lens case for holding soft contact lenses in accordance with the invention.
Figure 11:
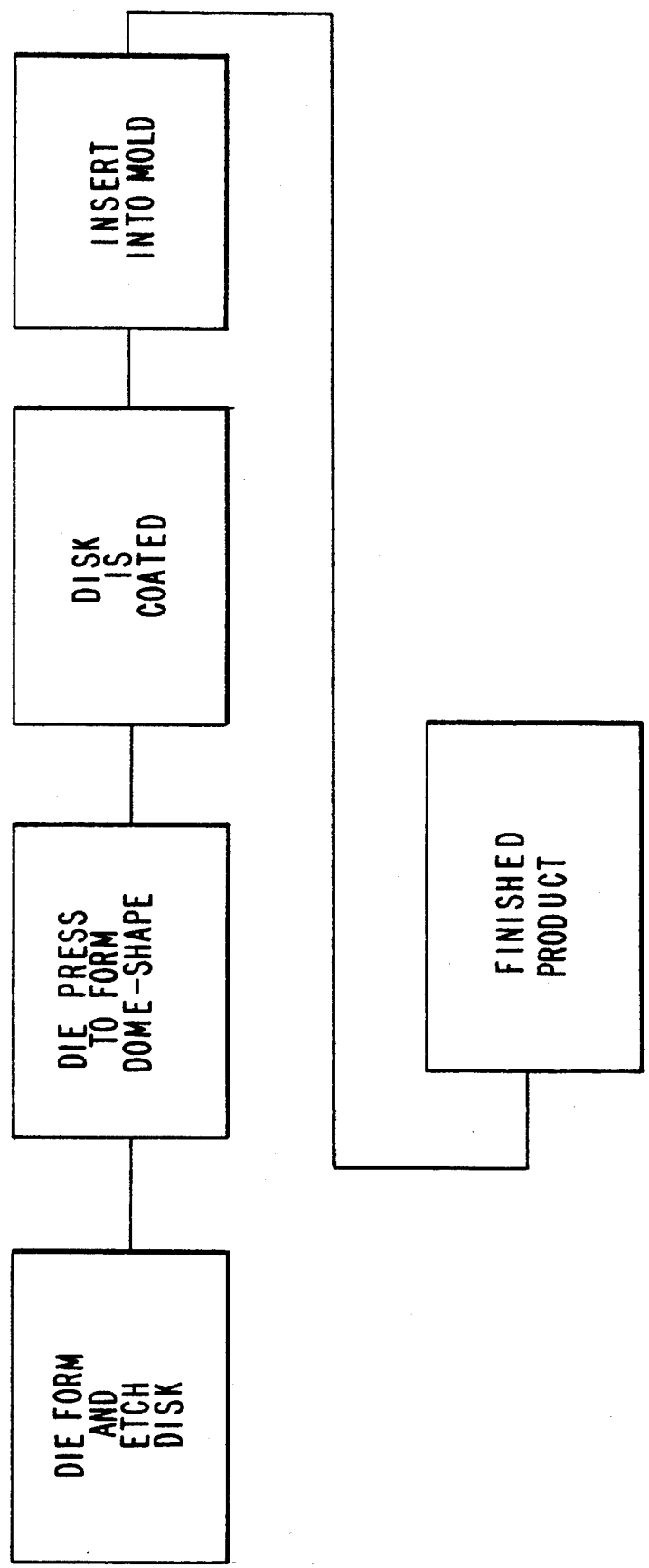
FIG. 11 is a flow chart showing the formation steps of the case in accordance with the invention.

Referring now to the drawings wherein like reference characters designate identical or corresponding parts throughout the several views, and more particularly to FIG. 1, an assembly for disinfecting soft contact lenses including a contact lens-receiving holder apparatus or case 16 in accordance with the invention comprises an assembly including a pouch 10 formed of material transparent to microwave electromagnetic radiation which contains a disinfecting solution such as saline solution 37, and a clamp 38 for closing the pouch. A case 16 in accordance with the invention and described in detail below, defines interior spaces or compartments adapted to receive the contact lenses to be disinfected and which are in fluid communication with the remainder of the pouch interior, but which are shielded from microwave radiation. The closed pouch assembly is supported on a fixture 54 within the cavity 51 of a conventional microwave oven 52 of the type commonly found in many households. The pouch 10 is formed of flexible sheet material comprising a laminate of polypropylene and polyester transparent to microwave electromagnetic radiation.

In the disinfection process, the case 16 with the contact lenses situated in respective compartments is introduced into the pouch 10 along with sufficient saline solution 37 to ensure that the case 16 is completely immersed in the solution, and the pouch 10 is then sealed by means of clamp 38. A vent (not shown) is provided in connection with the pouch to permit vapor to escape when a threshold internal pressure of the sealed pouch is exceeded. The assembly is then mounted on the fixture 54 and situated in the cavity 51 of the microwave oven 52. Fixture 54 comprises a base 56 from which a planar supporting wall 58 extends upwardly at an angle to the horizontal. The sealed assembly is supported on wall 58 by fastening clamp 38 to its top by any suitable means, such as by Velcro fasteners.

Irradiation of the assembly with microwave electromagnetic radiation then proceeds whereupon the saline disinfectant solution is heated under the thermal effects of the microwave radiation. However, the contact lenses 34 situated in the lens case compartments (FIG. 10) are shielded from the radiation. The heated disinfectant solution is in constant contact with the lenses and the lenses are disinfected by heat within a relatively short time.

The heat disinfection process described above is particularly advantageous in that a visual indication that disinfection is proceeding is provided. In particular, as the sealed pouch assembly is irradiated by microwave radiation, the disinfectant solution or saline solution 37 begins to vaporize. As the vapor pressure within pouch 10 increases, the pouch 10 expands to a distended condition to provide an easily recognizable visual indication that disinfection is proceeding. Vapor is vented from within the pouch when the internal pressure exceeds a certain threshold to eliminate any possibility of rupture of the pouch.

Another advantage of the process is that irradiation of the sealed assembly may continue until the disinfecting solution 37 itself is substantially disinfected and the pouch 10 can then be maintained in a sealed condition after completion of the irradiating step with the lenses in contact with the disinfectant solution. In this manner, the lenses are protected from recontamination until future use.

Generally, case 16 comprises a pair of substantially planar cover members 18,20 formed of polypropylene connected to each other by an integral hinge portion 22. A pair of dome-shaped members 24a,24b are affixed to each of the cover members 18,20 so that the dome-shaped portions of members 24 extend through openings 28 formed in the cover members 18,20 and protrude beyond the outer surface of the cover member (FIG. 8). When the lens case is closed as seen in FIGS. 9 and 10, the dome-shaped members cooperate to define compartments for receiving the contact lenses to be disinfected.

Each dome-shaped member 24 is formed from a substantially planar, thin metallic disc 50 as shown in FIG. 2. In the illustrated embodiment, disc 50 comprises No. 304 stainless steel sheet having a thickness of about 0.010 inches. For each case 16, four discs are initially die cut from a metallic sheet and etched to form a plurality of apertures 26. The apertures 26 extend through the thickness of disc 50 to allow disinfecting solution to pass into the lens-containing compartments during the disinfection process. However, the apertures are sufficiently small to prevent microwave radiation from passing therethrough. The apertures in the discs 50 are generally circular and preferably have a diameter of about 0.065 inches which is generally effective to prevent the passage of microwave radiation through the discs 50. As shown in FIG. 3, the apertures 26 are arranged in a central region of the disc 50 maintaining a non-apertured region 53 around the circular peripheral edge of the disc 50 sufficient to form mounting rim 30 as described below.

The apertured metallic disc 50 is fabricated by a photo-etching (photo chemical machining) process to insure burr-free parts to prevent the possibility of arcing in a microwave field. The photo chemical machining process employs light sensitive coatings and etching reagents to develop high precision, chemically machined parts which do not have sharp edges to prevent arcing in a microwave field.

The disc 50 is then die-pressed in a manner such that the central apertured region of disc 50 is provided with the dome-like shape while the non-apertured peripheral region 53 of the disc 50 is formed into either a peripheral mounting rim 30a including a circumferential groove to define a female dome-shaped member 24a or a peripheral mounting rim 30b including a circumferential projection to define a male dome-shaped member 24b (FIG. 10). As seen, for example in FIG. 7, a pair of female dome-shaped members 24a are affixed to cover member 18 and a pair of male dome-shaped members are affixed to cover member 20 so that each lens-receiving compartment 32 is defined by female and male dome-shaped members 24a,24b. The mounting rims 30a,30b of the male and female dome-shaped members 24a,24b that form each compartment 32 are designed to nest as shown in FIG. 10 when the case is closed. The portions of members 24a,24b situated inwardly of the nesting groove and projection form circular domes thereby aiding in the prevention of arcing of the dome-shaped members 24a,24b in a microwave field.

The stainless steel dome-shaped members are then coated with at least one layer 46, and preferably two, of a non-stick, heat, chip and corrosion resistant material of the type available from Whitford Corporation under the designation Ultralon OC-417. Similar material such as DuPont Teflon™ may also be used. Besides serving a cosmetic purpose to color match the dome portion to the plastic case, the coating allows the disinfected lenses to be more easily removed from the lens-receiving compartments 32. It also serves to protect lenses which may be placed in the disinfection unit without proper hydration, as well as to protect scratching of the lens surface which might occur one bare metal surface. The coating layer 46 is important since any exposed metallic parts of the dome-shaped members 24a,24b, after being incorporated into case 16, will cause arcing when placed in a microwave field.

After the dome-shaped members 24a,24b are coated, four tabs 44 shown in FIGS. 4, 5 and 10 are attached to each of the dome-shaped members 24a,24b at 90° intervals and deflected at an angle of from about 30° to about 45°.

Subsequently, the dome-shaped members 24a,24b with tabs 44 attached thereto are placed in an injection molding apparatus which will form the case 16 with the dome-shaped members 24a,24b incorporated therein. During the molding process, the tabs 44 on the dome-shaped members 24a,24b are embedded in the polypropylene of the case (FIG. 10) to thereby securely fasten each dome-shaped member 24a,24b in the case 16.

In another embodiment shown in FIG. 12, the disc 50 may comprise a metallic wire mesh material 55 at least in the central region thereof so that when the disc 50 is die-pressed, this central region of mesh material 55 will form the apertured dome of dome-shaped members 24a,24b.

As seen most clearly in FIG. 10, upon folding the cover members 18 and 20 into engagement with each other about hinge 22, the female dome-shaped member 24a affixed to cover member 18 moves into opposing relationship with a corresponding male dome-shaped member 24b affixed to cover member 20, with peripheral mounting rims 30b of member 24b nesting within the mounting rim 30a of opposing female dome-shaped members 24a to thereby define respective compartments 32 for receiving contact lenses 34. The nesting construction of the rims 30a,30b provides assurance that microwave radiation will not enter into the compartments through the seam formed between respective dome-shaped members.

The preferred dimensions of the case 16 is a 2.25 long by 1.25 wide and it is substantially rectangular. The dome-shaped members 24a,24b are dimensioned within this range and to receive a standard size contact lenses 34.

A closure device is provided in connection with the case 16 to ensure that the cover members 18,20, once closed together, remain in a closed position until removal of the contact lenses from the case is desired. In the illustrated embodiment, the closure device of the case 16 is a latching mechanism, i.e., tab 40, arranged on cover member 20 which snaps over a groove 42 arranged in cover member 18 when the case 16 is closed. Tab 40 extends outward from the side of cover member 20 and has a projection thereon which engages with groove 42 arranged in a face of cover member 18 to lock the cover members 18,20 to each other. Further, a tab 48 is located on one side of the top of the case 16, on cover member 18 as shown, and allows the case to be opened by the action of using the thumb and forefinger of one hand to grasp the case via tab 48 while the thumb of the other hand releases the closure. Thus, tab 48 is preferably placed on the cover member which does not have the tab 40 thereon but instead has the groove formed therein (FIG. 7).

In the use of the case in a heat disinfecting process, e.g., as described above with reference to FIG. 1, the contact lenses 34 are situated in the shielded compartments 32 of the holder apparatus or case 16 by placing each of them into the concave depression of a respective one of the pair of dome-shaped members 24a,24b, and then closing the holder apparatus as described above whereupon the lenses become situated in respective shielded compartments 32. The interior of the compartments 32 are shielded from exposure to microwave radiation by the metallic material of the dome-shaped members 24. The apertures 26 formed in the sheet material of the dome-shaped members 24a,24b provide fluid communication between the interior of compartments 32 and the remainder of the pouch interior so that disinfecting solution or saline solution 37 in the pouch fills the compartments 32 and contacts the lenses 34. However, the apertures 26 are sufficiently small that microwave electromagnetic radiation is prevented from passing into the interior of the compartments 32.

In a preferred embodiment, cover member 18 comprises two separated portions, 18A and 18B as shown in phantom lines in FIG. 6. Each portion 18A,18B has one of the dome-shaped members 24b mounted thereon which faces a respective mating one of the dome-shaped members in cover member 20. In this embodiment, it is possible to individually access each of the compartments 32 which may be designated as a right and left compartment for retaining a respective right and left contact lens. The notations "R" for right and "L" for left may also be marked on either cover member 18,20, the interior of cover member 18 as shown, or other suitable identification means may be provided on either one of the cover members 18,20.

Obviously, numerous modifications and variations of the present invention are possible in the light of the above teachings. For example, it is understood that the lens case in accordance with the invention may be used in other conventional heat disinfection processes, possibly in conjunction with a microwave, or even non-heat disinfection processes. It is therefore to be understood that within the scope of the claims appended hereto, the invention may be practiced otherwise than as specifically disclosed herein.

We claim:

1. A case for use in disinfecting soft contact lenses, comprising:

first and second substantially planar cover members;

first and second pairs of compartment-forming members structured to hold a pair of contact lenses in place and affixed to said first and second planar cover members respectively, said compartment-forming members comprising shielding means which present a barrier to the transmission of microwave electromagnetic radiation therethrough;

said first pair of compartment-forming members being positioned upon engagement of said first cover member and said second cover member into opposing relationship to said second pair of compartment-forming members to thereby form a pair of contact lens-receiving compartments having interiors in fluid communication with the ambient atmosphere; and wherein said shielding means comprise a metallic sheet material having a plurality of apertures, said apertures providing fluid communication between the interior of said contact lens-receiving compartments and the ambient atmosphere, and being sufficiently small to prevent passage of microwave electromagnetic radiation into the interior of said contact lens-receiving compartments.

2. Apparatus as recited in claim 1, wherein said compartment-forming members comprise dome-shaped members.

3. Apparatus as recited in claim 2, wherein each of said first pair of dome-shaped members comprises a circumferential groove to constitute a pair of male dome-shaped members and each of said second pair of dome-shaped members comprises a circumferential projection to constitute a pair of female dome-shaped members, said circumferential projections of said pair of male dome-shaped members nesting in a respective one of said circumferential grooves of said pair of female dome-shaped members.

4. Apparatus as recited in claim 2, wherein said second cover member comprises two separate portions, each of said portions comprising one of said second pair of compartment-forming members, whereby each of said pair of compartments is separately accessible.

5. Apparatus as recited in claim 1, further comprising tabs extending outwardly from a peripheral surface of said compartment-forming members to attach said compartment-forming members to said first and second cover members.

6. Apparatus as recited in claim 1, wherein said compartment-forming members are formed of a metallic sheet material having apertures at least in a central region thereof.

7. Apparatus as recited in claim 1, wherein said compartment-forming members are formed of metallic wire mesh material.

8. Apparatus as recited in claim 1, further comprising locking means for locking said first cover member in engagement with said second cover member.

9. Apparatus as recited in claim 8, wherein said locking means comprise a tab extending outward from an edge of said first member, said tab having a projection thereon, and a groove arranged in a face of said second member, said projection engaging with said groove to lock said first member to said second member.

10. Apparatus as recited in claim 1, further comprising identification means for identifying right and left ones of said pair of compartments.

11. Apparatus as recited in claim 1, further comprising at least one coating applied to said metallic sheet material to cover exposed metal surfaces thereof.

* * * * *